United States Patent

Patscheke et al.

[11] Patent Number: 5,538,894
[45] Date of Patent: Jul. 23, 1996

[54] AGENT FOR STABILIZING BLOOD

[76] Inventors: Heinrich Patscheke, MaximiLianstrasse 6, 76133 Karlsruhe; Andreas Ruf, Kirchbergstrasse 16, 76356 Weingarten, both of Germany

[21] Appl. No.: 299,784

[22] Filed: Sep. 1, 1994

[30] Foreign Application Priority Data

Sep. 7, 1993 [DE] Germany ............... 43 30 213.0

[51] Int. Cl.$^6$ ................... G01N 33/48
[52] U.S. Cl. ............... 436/18; 435/2; 435/40.5; 435/40.51
[58] Field of Search ............. 424/93 U–93AA, 424/529–534, 2; 436/18, 8, 16; 435/2

[56] References Cited

U.S. PATENT DOCUMENTS

| | | | |
|---|---|---|---|
| 4,107,287 | 8/1978 | Morton et al. | 424/8 |
| 4,361,552 | 11/1982 | Baur, Jr. | 424/105 |
| 4,751,179 | 6/1988 | Ledis et al. | 435/4 |

*Primary Examiner*—James C. Housel
*Assistant Examiner*—Rachel Heather Freed
*Attorney, Agent, or Firm*—Anderson Kill Olick & Oshinsky

[57] ABSTRACT

The present invention relates to an agent for stabilizing blood and comprises an aqueous solution of methacrolein and formaldehyde.

3 Claims, No Drawings

AGENT FOR STABILIZING BLOOD

FIELD OF INVENTION

The invention relates to an agent for stabilizing human, whole blood and blood cell preparations, preferably for the immunological determination of blood cell antigens with fluorescence-labeled antibodies.

BACKGROUND INFORMATION AND PRIOR ART

The blood group substances, which are mostly determined by conventional agglutination methods, belong to the classical blood cell antigens. On the other hand, antigens of the granulocytes, lymphocytes, monocytes and thrombocytes are largely determined at the present time by means of fluorescence-labeled antibodies. Not only are blood cells assigned unambiguously to the individual cell classes on the basis of their immunological properties, but their functional state is also characterized on the same basis. In medical diagnostics, therefore, immunocytometric methods have become widespread. At the present time, they serve to differentiate different forms of leukemia and lymphocytes and identify and evaluate defects in the immune system.

Monoclonal antibodies, labeled with different fluorochromes, are used to identify certain antigenic epitopes. Individual cells can be detected directly with a fluorescence microscope or a flow cytometer to indicate the presence of certain antigens. In indirect labeling, it is not the primary antibody, which recognizes the epitope in question, which has a fluorescent label, but a second antibody, which is directed against the protein of the primary antibody and bound by this. The immunotyping of blood cells with fluorescing antibodies is based at the present time particularly on flow cytometry, which permits thousands of individual cells to be analyzed in less than one minute and the fluorescence properties, as well as the characteristic light-scattering properties are determined for each cell. The fluorescence measurement serves to quantify the cell-bound antibodies. On the other hand, the light-scattering properties reflect morphological characteristics of the individual classes of cells. With flow cytometry therefore, statistically confirmed results can be achieved, the correctness of which is based on the partially automated, simultaneous evaluation of several cellular characteristics.

Since the efficient method of flow cytometry has been used in medical diagnosis, it has become increasingly clear that immunocytometric results depend appreciably on the functional state of the cells investigated. The expression of the antigens investigated depends namely to a large extent on the activation state of the cells and the effects of handling and keeping the blood sample or the cell preparation. For example, antigens are destroyed after a few hours by cellular proteases. The results are affected qualitatively and quantitatively by such pre-analytical effects. In the case of very rapidly reacting cells, such as the thrombocytes, dramatic changes in different surfaces/antigens are unavoidable if the cells are not stabilized immediately when the sample is taken. These interfering effects are particularly critical when the blood cells must be worked up or isolated before the measurement.

Therefore, for immunological phenotyping of blood cells and particularly for the quantitative analysis of antigen expression, it would be of appreciable benefit if the sample could be stabilized so that the pre-analytical changes in the cell antigens to be investigated are precluded. Such a procedure is indispensable for most of the questions relating to thrombocytes and necessary to quantify the antigen expression of granulocytes, monocytes, lymphocytes and erythrocytes. For the last-mentioned cells, this is true particularly when the samples cannot or should not be analyzed immediately after they are obtained.

The requirements, which a suitable stabilizing method should meet, that is, the so-called technical problem here, can be defined as follows:

Conditions 1 to 6

1. The cell metabolism should be interrupted sufficiently rapidly with the stabilizing agent so that a chemical cell stimulus, provided simultaneously, remains ineffective.
2. At the same time, the immunological properties of the cells basically should not be changed and, in particular, there should be no destruction of the antigens.
3. The morphological properties of the cells should be retained.
4. The autofluorescence of the cells should not increase.
5. The sample must not gel, so that it can continue to be supplied directly to flow-cytometric analysis.
6. The sample should be stable for at least 24 hours at room temperature.

No method, which fulfills these criteria, has previously been known. For blood cells other than thrombocytes, sample stabilization has been omitted up to now. However, in the course of national and international efforts at standardization, the request for stabilizing methods presumably becomes irrefusable also for blood cells other than thrombocytes. Up to now, methods, which fulfill different partial aspects of the above requirements, are in use for stabilizing thrombocytes. One method does no more than ensure anticoagulation with citrate (SHATTIL et al., 1987, GINSBERG et al., 1990); others use formaldehyde (GEORGE et al., 1986, TSCHOEPE 1992) or glutaraldehyde (NIEUWENHUIS et al., 1987; RUF and PATSCHEKE, 1993) for fixing cells.

It is impossible to prevent activation metabolism definitively with one anticoagulant alone (SHATTIL et al.). Reliable stabilization of the cell properties is not possible, so that the initial condition, No. 1, is not already fulfilled. Consequently, condition No. 3, namely morphological fixing, is also not fulfilled. On the other hand, such a procedure fulfills conditions 2, 4, and 5. Accordingly, flow-cytometric analysis of the thrombocytes is possible, however, only under strictly controlled conditions. It is possible to keep to such conditions in model in vitro experiments, but not, with sufficient reliability, when patient samples are analyzed.

Other methods use formaldehyde (GEORGE et al., 1% by weight of formaldehyde, TSCHOEPE: DIII/protocol with 0.5% by weight of formaldehyde) as decisive active component.

Formaldehyde is a proven fixative for morphological investigations. It has long been known that formaldehyde ensures a very rapid and effective interruption of the cell metabolism, also in the case of thrombocytes. Admittedly, methods based on formaldehyde fulfill condition No. 1. However, it is a decisive disadvantage of formaldehyde that it leads to antigen destruction, which cannot be stopped even if the formaldehyde is neutralized after a brief period of action. This is true for thrombocytes, for example, for the important antigens GMP-140=CD 62, CD 41a, CD 42a. Formaldehyde is thus excluded as a suitable reagent for general stabilization in immunocytometry. Other disadvantages of formaldehyde are relatively less significant. For example, it is immaterial that formaldehyde also does not stabilize the morphology reliably and leads to an increase in autofluorescence. A stabilizing agent, with formaldehyde as only active component, could be suitable only for antigens, which are not sensitive to formaldehyde. The above-mentioned antigens, tested by various researchers on thrombocytes, are sensitive to formaldehyde.

Glutaraldehyde is a different fixation agent, which has proven its value in morphology. Sufficient stabilization can be achieved with low concentrations of about 0.05% by weight without destruction of the various thrombocytic antigens (NIEUWENHUIS et al.; RUF and PATSCHEKE, 1993). However, it is a major disadvantage that glutaraldehyde increases the autofluorescence of thrombocytes and, even more, that of other blood cells. The increase in non-specific autofluorescence can then mask the specific fluorescence resulting from bound antibodies and make it impossible to evaluate a slight bonding of antibodies. This is so particularly when directly labeled, primary antibodies are used, for which there is no amplification of the fluorescence signal, such as is possible with indirect labeling methods. This greatly limits, especially, analyses of whole blood and other unpurified cell preparations, for which direct labeling methods come into consideration mainly in order to avoid interference from plasma immunoglobulins.

Previous attempts to find suitable agents for a stabilizing method show that the core problem lies in finding an agent, which is sufficiently effective for stabilizing the cell activity and cell morphology rapidly and reliably and, at the same time, does not destroy the antigens. In order to attain the first condition, the proteins, including the enzymes, controlling the cell metabolism, must be inactivated. However, even antigens have a protein nature or are protein components and should remain unchanged. The difficulty of achieving the one without having to accept the other is therefore not surprising. The specificity of the aimed-for stabilization method therefore evidently lies in inactivating proteins functionally without affecting their antigenic properties.

The following references are cited in the text above:
1. Shattil, S. J., Cunningham M., and Hoxie J. A.: Detection of activated platelets in whole blood using activation-dependent monoclonal antibodies and flow cytometry. Blood 70:307/315 (1987)
2. Ginsberg, M. H., Frelinger A. L., Lam, S. C.-T., Forsyth J., McMillan R., Plow E. F., and Shattil S. J.: Analysis of platelet aggregation disorders based on flow cytometric analysis of membrane glycoprotein IIb/IIIa with conformation-specific monoclonal antibodies. Blood 76:2017/2023 (1990)
3. George, J. N., Pickett E. B., Saucerman S., McEver R. P., Kunicki T. J., Kieffer N. and Newman P. J.: Platelet surface glycoproteins. Studies on resting and activated platelets and platelet membrane microparticles in normal subjects, and observations in patients during adult respiratory distress syndrome and cardiac surgery. J. Clin. Invest. 78:340–348 (1986)
4. Tschoepe, D.: Markeanalyse und Funktiontest an Thrombozyten. (Labeling analysis and function test on thrombocytes). In: Anwendungen der Durchflußzytometrie in der Laboratoriumsdiagnostik, 2. Regensburger Kurs, Sept. 1992 (Use of flow cytometry in laboratory diagnosis, Second Regensburg Course, Sept. 1992), University of Regensburg, Institute for Clinical Chemistry and Laboratory Medicine.
5. Nieuwenhuis, H. K., van Oosterhout, I. I. G., Rorieonuke, E., van Iwaarden, R. and Sixma, J. J.: Studies with a monoclonal antibody against activated platelets: evidence that a secreted MW 53,000 lysosome-like granule protein is exposed on the surface of activated platelets in the circulation. Blood 70: 838/845.
6. Ruf, A. and Patscheke, H.; Whole blood procedure for flow cytometric determination of platelet antigens. In: R. E. Scharf, K. J. Clemetson (editors) Flow Cytometry of the Megakaryocte-Platelet System. Elsevier, Amsterdam 1993.

OBJECT OF THE INVENTION

An object of the present invention is an agent for stabilizing blood and comprises an aqueous solution of methacrolein and formaldehyde.

The present invention provides an agent for stabilizing blood, which fulfills the 6 conditions named above for a pre-analytical stabilization of the samples.

The inventive agent is characterized in that it comprises an aqueous solution of methacrolein and formaldehyde. Preferred embodiments that the methacrolein is present in a concentration of 0.01 to 0.5% by weight and formaldehyde is present in a concentration of 0.01 to 0.1% by weight, both dissolved in aqueous buffer solutions having pH of 6.5 to 7.5 with an osmolality of 200 to 600 mosmol/Kg.

The agent further may contain a phosphate, piperazine or an acetate buffer or any combination of the three. It may further contain aldehydes and/or dialdehydes dissolved in buffer solutions.

The following is a procedure, by means of which the listed results can be attained with the inventive agent:
1. Sample Preparation:
   Stabilization
   Blood is
   a) taken from a compressed or not compressed cubital vein and, by means of a butterfly (with an internal diameter of 0.6 mm)
   b) transferred directly into the inventive agent.
      Mixing ratio of about 1:1, total volume, for example, 600 μL.
      Incubation for 5 minutes at room temperature.
   Immune Labeling
   The stabilized blood sample (5 μL) is added to 45 μL of phosphate buffer. Addition of primary antibody in saturated concentration. Volume ≦ 10 μL
   Incubation for 15 minutes at room temperature.
   direct:
   addition of 450 μL phosphate buffer
   indirect:
   Addition of 150 μL phosphate buffer.
   Addition of secondary fluorochrome-coupled F(ab') fragments in saturated concentration: volume ≦ 20 μL.
   Incubation for 20 minutes at room temperature.
   Addition of 300 μL phosphate buffer.
2. Measurement:
   Flow-Cytometric Determination by the Usual Method.
   a) Instead of whole blood, it is possible to stabilize, in the same way, blood cell preparations, such as mononuclear cells and granulocytes, the concentration of which was increased by gradient centrifugation, washed and filtered thrombocytes, platelet-rich plasma, highly concentrated platelets, erythrocyte concentrates, cell fractions after plasmapheresis including stem cell preparations. The same applies for whole blood after a lysis treatment to destroy erythrocytes before an analysis of the leukocyte fraction.
   b) The sample can be mixed with the inventive agent also with other equipment, such as pipettes or syringes.

A closer characterization of the properties of the inventive blood-stabilizing agent follows:

For the reasons given above, the thrombocytes make the highest demands on the fixation agent. They react particularly rapidly to numerous chemical and physical stimuli with exposure of neoantigens or changes in the antigen pattern at their surface. At the same time, they undergo a change in shape from the disk shape to a spheroidal shape with pseudopodia, which can be quantified easily (MILTON and FROJMOVIC, 1979). As the smallest blood cells, they also make particularly high demands on the sensitivity and quality of the measurement method. The capability of the present invention is documented here, particularly for thrombocytes, it being understood that this is by way of illustration only and no limitation is intended.

In particular, the properties of the method were tested as follows:

Concerning Condition 1:

The change in shape of the thrombocytes is one of the most sensitive reactions of the thrombocytes to a stimulation, diskocytes changing into spheroechinocytes. It can be detected by a microscopic method (MILTON and FROJMOVIC; 1979) and is particularly suitable for checking the reliable and rapid interruption of cell activity. There should be no change in shape, even if the stabilizing reagent is added simultaneously with a strong stimulus, such as 1 μmole/L of the thromboxane mimetic U 46619 or 10 μmole/L of ADP.

There should be no response of the thrombocytes particularly when the stabilizing reagent was added before the stimulus. When added subsequently, the stabilizing reagent should stop the reaction at the precise time. All of these conditions are fulfilled by the application method given for the inventive agent.

Concerning Condition 2:

The antigen expression of CD 61, CD 41a, CD 42a, CD 62 and CD 63 (monoclonal antibodies of the DIANOVA company, Hamburg, and the Becton Dickinson company, Heidelberg) was measured on thrombocytes, which had not been stabilized, and on thrombocytes at different times after their stabilization with the inventive agent. The thrombocytes were or were not stimulated. Antigen destruction was not observed. With neutrophilic granulocytes, monocytes and lymphocytes, which had not been stimulated, appropriate experiments were carried out for the following antigens: CD 14 for monocytes, CD 3, CD 4, CD 8 for lymphocytes. The cells were used only in the unstimulated state. No change was observed in the expression of antigens.

Concerning Condition 3:

It is known that thrombocytes, fixed with formaldehyde, have a membrane vesiculation at their surfaces (see FIG. 2). Such a vesiculation can be recognized readily under the interference contrast microscope or the phase contrast microscope and increases with time. It affects the rheooptical properties of the thrombocytes and, with that, the scattered light pattern in the flow cytometer. There is no such change in the thrombocytes stabilized with the inventive agent.

Concerning Condition 4:

The increase in autofluorescence, associated with glutaraldehyde fixation, particularly of leukocytes and thrombocytes, is a decisive disadvantage. It makes the flow-cytometric measurement of a weak antigen expression impossible (see under 2.). The inventive agent does not increase the autofluorescence of thrombocytes or leukocytes to an interfering extent.

Concerning Condition 5:

Above a final concentration of about 0.5% by weight in whole blood samples, glutaraldehyde easily leads to gelling due to cross linking of the plasma proteins. Such samples cannot be used, especially not for flow-cytometric analyses. The inventive agent does not have this effect.

Concerning Condition 6:

All of the criteria, named above, were fulfilled by samples, which had been stabilized with the inventive agent and kept for at least 24 hours.

The following is named as reference in this connection: Milton, J. G., and M. M. Frojmovic: Shape-changing agents produce abnormally large platelets in a hereditary "giant platelets syndrome (MPS)". J. Lab. Clin. Med. 93:154–161 (1979).

In summarizing, the following may be noted.

Pursuant to the invention, solutions containing methacrolein and formaldehyde are produced which, after they are mixed with human whole blood, bring about a stabilization of the blood cells, contained therein, particularly of the erythrocytes, thrombocytes, granulocytes and lymphocytes, including their subclasses and immature preliminary stages, the following criteria being fulfilled:

a) Immediate interruption of the cellular metabolic activity. This is confirmed owing to the fact that native, discoid thrombocytes, unlike the control, do not react by a shape change to 10 μmoles/L of ADP, if stabilizing solution is added simultaneously with the ADP.

b) No destruction of the cell antigens. This is confirmed by 3 or more monoclonal antibodies, the expression of which is quantitatively the same in fixed and non-fixed samples.

c) Morphological fixation of the cells. This is confirmed due to the fact that stabilized thrombocytes do not form any membrane vesicles at their surface, which can be detected by means of an interference contrast microscope or a phase contrast microscope. Thrombocytes, which are fixed with formaldehyde having a final concentration of 1% by weight and generally showing vesiculation, serve as positive control for depicting membrane vesicles.

d) No interfering increase in the autofluorescence of the cells. This can be confirmed in a flow cytometer with an argon laser for the usually measured green and red fluorescence.

e) No gelling of the sample.

f) The criteria b) to e) are retained also after the sample has been kept for 24 hours at room temperature.

The inventive agent for stabilizing blood can be used for whole blood and other blood cell preparations, particularly for mononuclear cells and granulocytes, the concentration of which is increased by gradient centrifugation, whole blood after a lysis treatment for destroying erythrocytes, washed and filtered thrombocytes, platelet-rich plasma, highly concentrated platelets, erythrocyte concentrates and cell fractions after plasmapheresis, including stem cell preparations.

Moreover, instead of whole blood, cultured cells, such as cells of permanent cell lines, such as HL-60 cells, U-937, Hep-G2 cells, cells of primary cell cultures such as fibroblasts, endothelial cells from umbilical veins and cells from primary cell cultures, can also be stabilized with the inventive agent.

Finally, instead of whole blood, cell fragments such as microsomes and microparticles, can also be stabilized with the inventive agent.

We claim:

1. An agent for stabilizing blood without any negative impact on the antigenic properties of a blood cell, comprising an aqueous buffer solution of methacrolein and formaldehyde, said aqueous buffer solution having a pH of 6.5 to 7.5 with an osmolality of 200 to 600 mosmol/kg, said methacrolein being present in a concentration of 0.01 to 0.5% by weight and said formaldehyde being present in a concentration of 0.01 to 0.1% by weight.

2. The agent for stabilizing blood of claim 1, further comprising that said agent contains a buffer selected from the group consisting of a phosphate buffer, a piperazine buffer, an acetate buffer and any combination thereof.

3. The agent for stabilizing blood of claim 1, further comprising that said agent contains aldehydes, dialdehydes, or both dissolved in buffer solutions.

* * * * *